United States Patent
Lu

(10) Patent No.: US 11,028,421 B2
(45) Date of Patent: Jun. 8, 2021

(54) **RECOMBINANT *PSEUDOMONAS PLECOGLOSSICIDA* FOR PRODUCING L-XYLOSE AND APPLICATION THEREOF**

(71) Applicant: LINKCHEM CO. LTD., Shanghai (CN)

(72) Inventor: Xi Lu, Shanghai (CN)

(73) Assignee: LINKCHEM CO. LTD., Shanghai (CN)

( * ) Notice: Subject to any disclaimer, the term of this patent is extended or adjusted under 35 U.S.C. 154(b) by 0 days.

(21) Appl. No.: 16/699,052

(22) Filed: Nov. 28, 2019

(65) Prior Publication Data
US 2020/0109424 A1     Apr. 9, 2020

Related U.S. Application Data

(63) Continuation of application No. PCT/CN2019/082860, filed on Apr. 16, 2019.

(30) Foreign Application Priority Data

Aug. 20, 2018 (CN) .......................... 201810948746.3

(51) Int. Cl.
| | |
|---|---|
| C12P 19/02 | (2006.01) |
| C12N 15/52 | (2006.01) |
| C12N 1/21 | (2006.01) |
| C12N 15/78 | (2006.01) |
| C12N 1/20 | (2006.01) |
| C12N 9/88 | (2006.01) |
| C12N 9/04 | (2006.01) |

(52) U.S. Cl.
CPC ............... *C12P 19/02* (2013.01); *C12N 1/20* (2013.01); *C12N 15/52* (2013.01); *C12N 15/78* (2013.01); *C12N 9/0006* (2013.01); *C12N 9/88* (2013.01); *C12Y 101/99004* (2013.01); *C12Y 401/01001* (2013.01)

(58) Field of Classification Search
None
See application file for complete search history.

(56) References Cited

U.S. PATENT DOCUMENTS

2005/0239174 A1* 10/2005 Bao .......................... C12Q 1/32
                                                                      435/105

FOREIGN PATENT DOCUMENTS

| CN | 107312766 A | 11/2017 |
|---|---|---|
| CN | 108165591 A | 6/2018 |
| CN | 109055292 A | 12/2018 |
| WO | 2005017099 A3 | 6/2009 |

OTHER PUBLICATIONS

S.P. Lim et al. "Flexible Exportation Mechanisms of Arthrfactin in *Pseudomonas* sp. MIS38", J. Applied Microbiology 106: 157-166 (Year: 2009).*
M.E. Kovach et al. "Four New Derivatives of the Broad Host Range Cloning Vector pBBR1MCS Carrying Different Antibiotic Resistance Cassettes", Gene 166: 175-176 (Year: 1955).*
CGMCC Catalog entry for Strain CGMCC 1.12685 (Year: 2013).*
N. Kataoka et al. "Efficient Production of 2,5-Diketo-D-Gluconate via Heterologous Expression of 2-Ketogluconate Dehydrogenase in Gluconobacter japonicus", Applied and Environmental Microbiology 81(10): 3552-3560 (Year: 2015).*
D.M. Wang et al. "Purification, characterization and gene identification of a membrane-bound glucose dehydrogenase from 2-keto-D-gluconic acid industrial producing strain Pseudomonas plecoglossicida JUIM01", International Journal of Biological Macromolecules 118: 534-541 Jun. 2018. (Year: 2018).*

* cited by examiner

Primary Examiner — Rebecca E Prouty
(74) Attorney, Agent, or Firm — IPro, PLLC

(57) ABSTRACT

The disclosure discloses recombinant *Pseudomonas plecoglossicida* for producing L-xylose and application thereof, and belongs to the technical field of bioengineering. According to the disclosure, a synthesized 2-ketogluconate reductase gene and a 2,5-diketogluconate reductase gene derived from *Corynebaterium* ATCC 31090 and a pyruvate decarboxylase gene derived from *Saccharomyces cerevisiae* are successfully expressed in a host *P. plecoglossicida* by a double plasmid system, and an obtained genetically engineered strain is fermented for 56 h in a shake flask, where the yield of L-xylose reaches 16.2 g/L, and the transformation rate reaches 20.3%; the obtained genetically engineered strain is fermented for 48 h and 44 h in 3 L and 15 L fermentors, respectively, where the yields of L-xylose reach 37.6 g/L and 45.8 g/L, respectively, and the glucose transformation rates are 47.0% and 57.3%, respectively. The method has the advantages of low raw material cost, no pollution to the environment, simple operation, and important economic and social benefits.

8 Claims, 2 Drawing Sheets
Specification includes a Sequence Listing.

RECOMBINANT *PSEUDOMONAS PLECOGLOSSICIDA* FOR PRODUCING L-XYLOSE AND APPLICATION THEREOF

TECHNICAL FIELD

The disclosure herein relates to the field of recombinant *Pseudomonas plecoglossicida* for producing L-xylose and application thereof, and belongs to the technical field of bioengineering.

BACKGROUND

Xylose is a pentose, and L-xylose is mainly found in plants and animals. The xylose is a non-caloric sweetener widely used in food, medicine, chemical and other fields. Eating the xylose can improve the microbial environment of the human body and improve the body's immunity. The xylose is an ideal sweetener for diabetics.

At present, the xylose is prepared by extraction by an acid method, and the acid method for producing the xylose mostly adopts sulfuric acid for hydrolysis. However, the acid method for producing the xylose has the following disadvantages that: 1. a large amount of sulfuric acid is used in the production process, cellulose, hemicellulose and other carbohydrates in raw materials are hydrolyzed by the sulfuric acid, and a variety of by-products are produced, thereby affecting the post-extraction process and product quality; 2. in extraction of the xylose by the acid method, due to the addition of a large amount of strong acid and alkali liquid in the production process, a large amount of production waste liquid is produced in the production process, which causes great pollution to the environment; and 3 due to the presence of many impurities in acid-hydrolyzed sugar liquid, the post-treatment efficiency is low, many chemical processes are needed, the requirements on equipment are high, and the environmental protection cost is increased.

At present, the L-xylose is mainly produced by a chemical synthesis method, which has the above disadvantage. The L-xylose can also be produced by transformation of L-xylulose, but the L-xylulose is a rare sugar which is high in price, and is not suitable for serving as a raw material for producing the L-xylose.

*Pseudomonas plecoglossicida* belongs to *Pseudomonas* and is Gram-negative *bacillus*. The metabolism of glucose in *Pseudomonas* is accomplished by an ED pathway (Entner-Doudoroff pathway). Under aerobic conditions, the glucose is oxidized into gluconic acid in a periplasmic space. Studies have shown that most of gluconic acid (about 90%) produced by the glucose in *Pseudomonas* is transformed into 2-ketogluconic acid (2KGA). At present, *Pseudomonas plecoglossicida* is the main industrial strain for producing 2KGA in China.

SUMMARY

The disclosure provides recombinant *Pseudomonas plecoglossicida* for producing L-xylose. The recombinant *P. plecoglossicida* can directly utilize glucose to produce the L-xylose, the process is simple in operation, the product quality is high and there is no pollution to the environment.

A first object of the disclosure is to provide a recombinant strain for producing L-xylose. *P. plecoglossicida* is used as a host, and a double plasmid expression system is utilized to express a 2-ketogluconate dehydrogenase gene, 2,5-diketogluconate reductase gene and a pyruvate decarboxylase gene.

In an embodiment of the disclosure, the double plasmid expression system includes a plasmid pME6032 and a plasmid pBBR1MCS-2.

In an embodiment of the disclosure, the plasmid pME6032 is used for expressing the 2-ketogluconate dehydrogenase gene.

In an embodiment of the disclosure, the plasmid pBBR1MCS-2 is used for expressing the 2,5-diketogluconate reductase gene and the pyruvate decarboxylase gene.

In an embodiment of the disclosure, the 2-ketogluconate dehydrogenase gene 2GADH consists of three subunits, which are expressed as 2GADH-1, 2GADH-2, and 2GADH-3, respectively, and sequences of the subunits are respectively shown in SEQ ID NO. 1, SEQ ID NO. 2, and SEQ ID NO. 3; by using the plasmid pME6032 as a vector, the three subunits of 2GADH shown in SEQ ID NO. 1, SEQ ID NO. 2, and SEQ ID NO. 3 are expressed in the *P. plecoglossicida*.

In an implementation of the disclosure, the 2,5-diketogluconate reductase gene 2,5DKG is from *Corynebaterium* ATCC 31090.

In an implementation of the disclosure, the pyruvate decarboxylase gene PDC is from *Saccharomyces cerevisiae*.

In an implementation of the disclosure, the *P. plecoglossicida* host includes any one of *Pseudomonas plecoglossicida* CG MCC 7150, *Pseudomonas plecoglossicida* CG MCC 1.16111, *Pseudomonas plecoglossicida* CG MCC 1.12685, and *Pseudomonas plecoglossicida* CGMCC 1.761.

A second object of the disclosure is to provide a method for constructing the recombinant *Pseudomonas plecoglossicida* for producing L-xylose. The construction method includes the following specific steps:

(1) synthesizing a gene shown in SEQ ID NO. 1, SEQ ID NO. 2 and SEQ ID NO. 3 by a chemical method, and simultaneously ligating the above sequences to a vector pME6032 to form a recombinant plasmid pME6032-2gadh;

(2) transforming the recombinant plasmid pME6032-2gadh obtained in step (1) into the *P. plecoglossicida* to obtain single plasmid-containing recombinant *P. plecoglossicida*;

(3) respectively amplifying a 2,5-diketogluconate reductase gene and a pyruvate decarboxylase gene, and simultaneously ligating the above genes to a vector pBBR1MCS-2 to form a recombinant plasmid pBBR1MCS-2-25dkg-pdc; and (4) further transforming the recombinant plasmid pBBR1MCS-2-25dkg-pdc obtained in step (3) into the *P. plecoglossicida* containing the recombinant plasmid pME6032-2gadh obtained in step (2) to obtain double plasmid-containing recombinant *P. plecoglossicida*.

A third object of the disclosure is to provide application of the above double plasmid-containing recombinant *P. plecoglossicida* in production of L-xylose, including: culturing the recombinant strain until $OD_{650}$ is 0.6 to 0.8, adding IPTG to induce the expression of a 2-ketogluconate dehydrogenase gene, a 2,5-diketogluconate reductase gene and a pyruvate decarboxylase gene, and synthesizing the L-xylose by using glucose as a substrate.

Further, a seed medium in the application includes: glucose: 14.0 to 15.0 g/L, corn steep liquor: 3.5 to 4.0 g/L, urea: 1.5 to 2.5 g/L, $KH_2PO_4$: 1.5 to 2.5 g/L, $MgSO_4 \cdot 7H_2O$: 0.4 to 0.6 g/L, $CaCO_3$: 0.8 to 1.2 g/L, and has a pH value of 7.0; a fermentation medium in the application includes: glucose: 75.0 to 85.0 g/L, corn steep liquor: 3.0 to 4.0 g/L, urea: 1.5 to 2.5 g/L, $KH_2PO_4$: 1.5 to 2.5 g/L, $MgSO_4 \cdot 7H_2O$: 0.4 to 0.6 g/L, $CaCO_3$: 9.0 to 11.0 g/L, and has a pH value of 6.8.

A fourth object of the disclosure is to provide a method for producing xylitol, including: first producing L-xylose by applying the recombinant strain according to any one of claims 1 to 5 to produce L-xylose by synthesis using glucose as a substrate, and then utilizing saccharomycetes to transform the L-xylose into the xylitol.

The disclosure has the following beneficial effects:

(1) the *P. plecoglossicida* is the main industrial strain for producing 2-ketogluconic acid (2KGA) in China, which can achieve a higher sugar acid transformation rate in industrial production; by adopting the method provided by the disclosure, the 2-ketogluconic acid can produce the L-xylose under the catalysis of 2-ketogluconate dehydrogenase, 2,5-diketogluconate reductase and pyruvate decarboxylase, thereby providing new raw materials and methods for L-xylose production.

(2) The process for producing L-xylose by a fermentation method is simple in operation, and has no pollution to the environment, the glucose is used as the substrate, and is fermented for 56 h in a shake flask, and the yield of L-xylose can reach 16.2 g/L, the transformation rate reaches 20.3%, the fermentation is carried out for 48 h and 44 h on 3 L and 15 L fermentors respectively, the yield of L-xylose can reach 37.6 g/L and 45.8 g/L, respectively, and the glucose transformation rate is 47.0% and 57.3%, respectively.

(3) The method provided by the disclosure can be directly used for a biotransformation experiment of the saccharomycetes, and is used for producing xylitol, and the method does not need detoxification, has a good fermentation performance, and is favorable for transforming xylose into xylitol. Therefore, the method for preparing L-xylose provided by the disclosure lays a foundation for green industrial production in the future.

DETAILED DESCRIPTION

Figure 1:
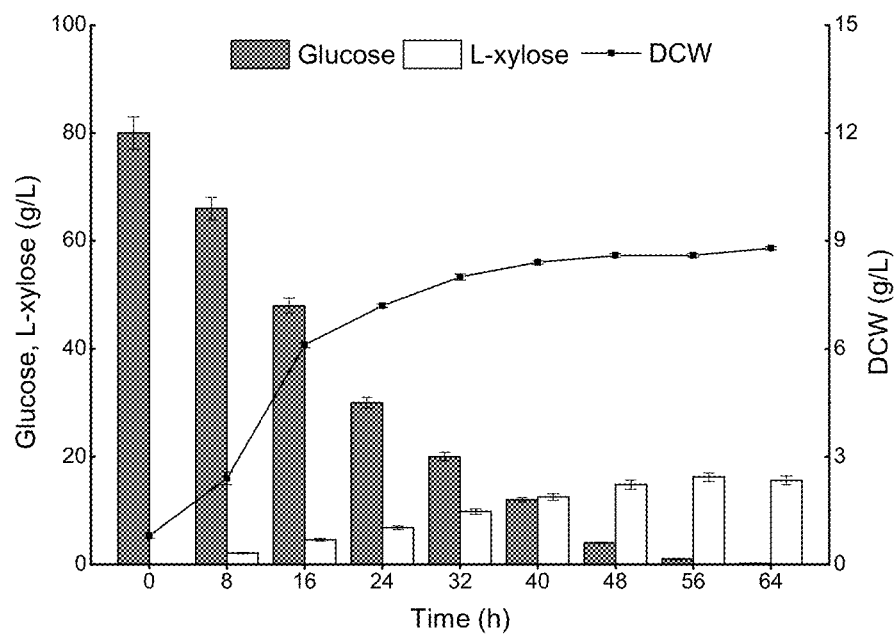
FIG. 1 shows results of fermentation of a recombinant strain *P. plecoglossicida*-2gadh-25dkg-pdc in a shake flask.

For the purpose of making objects, characteristics and advantages of the disclosure more clear and understandable, the detailed descriptions will be made to the specific implementations of the disclosure in conjunction with specific embodiments.

The concentration of L-xylose is determined by high performance liquid chromatography. The high performance liquid chromatography conditions are as follows: chromatographic column: HPX-87H (Bio-Rad Hercules), column temperature: 35° C.; detector: refractive index detector; mobile phase: 5 mM $H_2SO_4$, and flow rate: 0.6 mL/min. A fermentation supernatant was filtered by 0.22 μm micropores to remove impurities and then directly used for the detection of L-xylose.

The concentration of glucose is determined by a domestic SBA-40C biosensor analyzer.

A calculation method of glucose transformation rate: glucose transformation rate=total amount of glucosamine/total sugar consumption*100%.

A sequence of a subunit 1 of a 2-ketogluconate dehydrogenase gene 2GADH is shown in SEQ ID NO. 1.

A sequence of a subunit 2 of the 2-ketogluconate dehydrogenase gene 2GADH is shown in SEQ ID NO. 2.

A sequence of a subunit 3 of the 2-ketogluconate dehydrogenase gene 2GADH is shown in SEQ ID NO. 3.

Primers are shown in Table 1.

TABLE 1

Associated primers

| Name | F/R | Primer sequence (5'-3') | Sequence number |
|---|---|---|---|
| 2GADH-1 | F | CGC*GAATTC*ATGAACCTGAAAA TCGAACCGGA | SEQ ID NO. 4 |
|  | R | CCC*GAGCTC*TTACAGGTTTTCA ATCAGAGACGG | SEQ ID NO. 5 |
| 2GADH-2 | F | CGC*GAGCTC*GATGAAAAAACCG GTTTTCACCGCG | SEQ ID NO. 6 |
|  | R | CCC*GGTACC*TCATGCATCACCT TTCATACGCAGGC | SEQ ID NO. 7 |
| 2GADH-3 | F | CGC*GGTACC*GATGAAACAGCTG CTGATGGCAA | SEQ ID NO. 8 |
|  | R | CTG*CCATGG*TTAACCGTTATCA CGCGCGA | SEQ ID NO. 9 |
| 2,5DKG | F | CGC*GGTACC*GATGAATCTAAAA ATCGAACCCGACGTAATTTTTT | SEQ ID NO. 10 |
|  | R | ACGC*GAATTC*TCATCCATTGTC TCGGGCTATCC | SEQ ID NO. 11 |
| PDC | F | CATG*GAAATTC*ATTCAATTACT TTGGGTAAATATTTGTTCG | SEQ ID NO. 12 |
|  | R | CCG*GGATCC*TTGCTTAGCGTTG GTAGCAGCAGTC | SEQ ID NO. 13 |

Embodiment 1

(1) Construction and Identification of Recombinant Plasmid pME6032-2Gadh

Sequences shown in SEQ ID NO. 1, SEQ ID NO. 2, and SEQ ID NO. 3 were obtained by chemical synthesis, and primers (2GADH-1, 2GADH-2, and 2GADH-3, see Table 1) were designed. A gene of three subunits of a ketogluconate dehydrogenase gene (2GADH) was sequentially ligated on a plasmid pME6032 at a temperature of 16° C. overnight at restriction enzyme cutting sites EcoRI, SacI, KpnI, and NcoI, and a ligation product pME6032-gadh was transformed by a chemical method into *Escherichia coli* JM109 competent cells. The obtained transformation liquid was applied onto a 50 mg/L tetracycline-containing LB plate, and the recombinant plasmid pME6032-2gadh constructed was verified by extracting and sequencing the plasmid.

(2) Construction of Recombinant Strain *P. plecoglossicida*-2Gadh

The plasmid pME6032-2gadh constructed in step (1) was transformed into an original strain *Pseudomonas. plecoglossicida* CGMCC 7150 by an electrotransformation method, and a positive strain *P. plecoglossicida*-2gadh was obtained by screening with tetracycline.

(3) Construction and identification of recombinant plasmid pBBR1MCS-2-25dkg-pdc

Primers (2,5DKG and PDC, see Table 1) were designed using *Corynebaterium* ATCC 31090 and *Saccharomyces cerevisiae* genomes as templates, respectively, a 2,5-diketogluconate reductase gene (2,5DKG) and a pyruvate decarboxylase gene (PDC) were amplified, the 2,5-diketogluconate reductase gene and the pyruvate decarboxylase gene were sequentially ligated on a plasmid pBBR1MCS-2 at a temperature of 16° C. overnight at restriction enzyme cutting sites KpnI, EcoRI, and BamHI, and a ligation product pBBR1MCS-2-25dkg-pdc was transformed into the *E. coli* JM109 competent cells by a chemical method. The obtained transformation liquid was applied onto a 50 mg/L kanamycin-containing LB plate and the recombinant plasmid pBBR1MCS-2-25dkg-pdc was verified by extracting and sequencing the plasmid.

(4) Construction of Recombinant Strain *P. plecoglossicida*-2Gadh-25Dkg-Pdc

The plasmid pBBR1MCS-2-25dkg-pdc constructed in step (3) was transformed into the strain *P. plecoglossicida*-2gadh obtained in step (2) by an electrotransformation method, and a positive strain *P. plecoglossicida*-2gadh-25dkg-pdc was obtained by screening with ampicillin.

Embodiment 2

An original strain was *Pseudomonas plecoglossicida* CGMCC 1.12685, the remaining steps were the same as in Embodiment 1, and a positive recombinant strain *P. plecoglossicida* 1-2gadh-25dkg-pdc was obtained by screening.

Embodiment 3

Culture of Recombinant Strain *P. plecoglossicida*-2gadh-25dkg-pdc and L-xylose Fermentation Seed medium: glucose: 15.0 g/L, corn steep liquor: 4.0 g/L, urea: 2.0 g/L, $KH_2PO_4$: 2.0 g/L, 0.5 g/L, $CaCO_3$: 1.0 g/L, and pH value: 7.0.

Fermentation medium: glucose 80.0 g/L, corn steep liquor: 4.0 g/L, urea 2.0 g/L, $KH_2PO_4$: 2.0 g/L, $MgSO_4 \cdot 7H_2O$: 0.5 g/L, $CaCO_3$: 10.0 g/L, and pH value: 6.8.

Shake flask culture: a suitable amount of suspension of strain (the recombinant strain obtained in Embodiment 1) was inoculated into a 500 mL shake flask containing 50 mL of seed medium, cultured at a temperature of 30° C. and a rate of 220 r/min for 16 to 20 h, and transferred to a 500 mL shake flask containing 50 mL of fermentation medium at an inoculation amount of 10%; when the strain was cultured at the temperature of 30° C. and the rate of 220 r/min until $OD_{650}$ was 0.6, IPTG was used for induction, where the final concentration of IPTG was 0.5 mM, and the induction temperature was 25° C., fermentation was carried out for 64 h, and samples were taken periodically.

The yield of L-xylose was determined. The results are shown in FIG. 1. It can be seen that at the 56th h of the fermentation, the total amount of L-xylose produced by the recombinant strain *P. plecoglossicida*-2gadh-25dkg-pdc reached a maximum value of 16.2 g/L, and the glucose transformation rate was 20.3%.

Embodiment 4

Fermentation of Recombinant Strain *P. plecoglossicida*-2gadh-25dkg-pdc in 3 L Fermentor A fermentation medium and conditions of a 3 L fermentor are as follows:

Fermentation medium: glucose: 80.0 g/L, corn steep liquor: 4.0 g/L, urea: 2.0 g/L, $KH_2PO_4$: 2.0 g/L, $MgSO_4 \cdot 7H_2O$: 0.5 g/L, $CaCO_3$: 10.0 g/L, and pH value: 6.8.

Fermentation conditions: the initial liquid volume was 2.0 L, and the seed inoculation amount was 10%. Initial fermentation conditions: the culture temperature was 30° C., pH was 6.8, the stirring rate was 400 rpm, the ventilation volume was 1.5 vvm, when the $OD_{650}$ of a thallus was 0.6, IPTG was used for induction, where the final concentration of IPTG was 0.5 mM, and the induction temperature was 25° C., the fermentation was carried out for 64 h, and samples were taken periodically.

Figure 2:
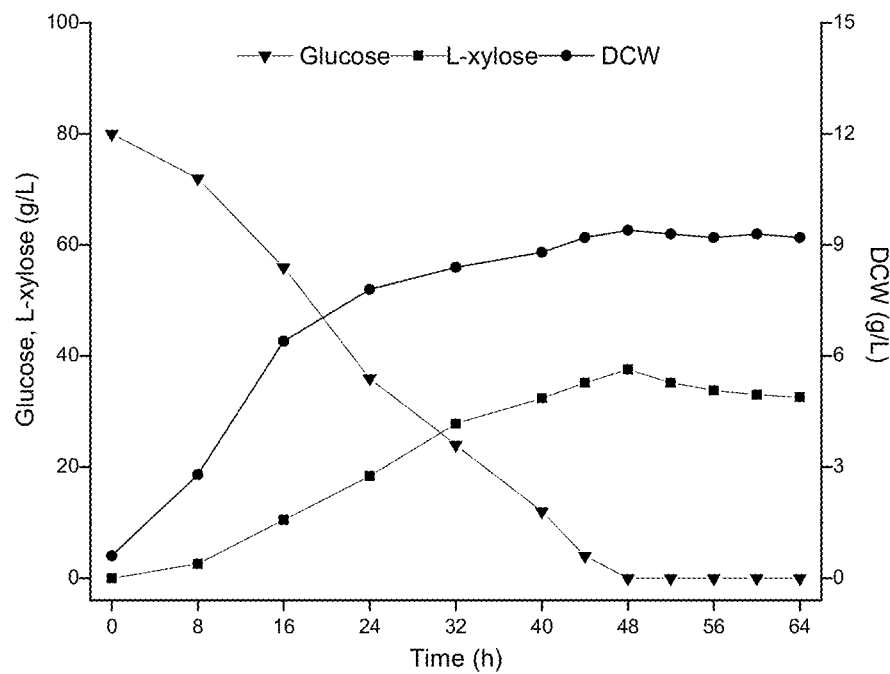
FIG. 2 shows results of batch fermentation of a recombinant strain *P. plecoglossicida*-2gadh-25dkg-pdc in a 3 L fermentor.

The yield of L-xylose was determined. The results are shown in FIG. 2. It can be seen that at the 48th h of the fermentation, total amount of L-xylose produced by the recombinant strain *P. plecoglossicida*-2gadh-25dkg-pdc reached a maximum value of 37.6 g/L, and the glucose transformation rate was 47.0%.

Embodiment 5

Fermentation of Recombinant Strain *P. plecoglossicida*-2gadh-25dkg-pdc in 15 L Fermentor A fermentation medium and conditions of a 15 L fermentor were as follows:

Fermentation medium: glucose: 80.0 g/L, corn steep liquor: 4.0 g/L, urea: 2.0 g/L, $KH_2PO_4$: 2.0 g/L, $MgSO_4 \cdot 7H_2O$: 0.5 g/L, CaCO3: 10.0 g/L, and pH value: 6.8.

Fermentation conditions: the initial liquid volume was 10.0 L, and the seed inoculation amount was 10%. Initial fermentation conditions: the culture temperature was 30° C., pH was 6.8, the stirring rate was 400 rpm, the ventilation volume was 0.8 vvm, the fermentor pressure was 0.5 bar, when the $OD_{650}$ of a thallus was 0.6, IPTG was used for induction, where the final concentration of IPTG was 0.5 mM, and the induction temperature was 25° C., the fermentation was carried out for 64 h, and samples were taken periodically.

Figure 3:
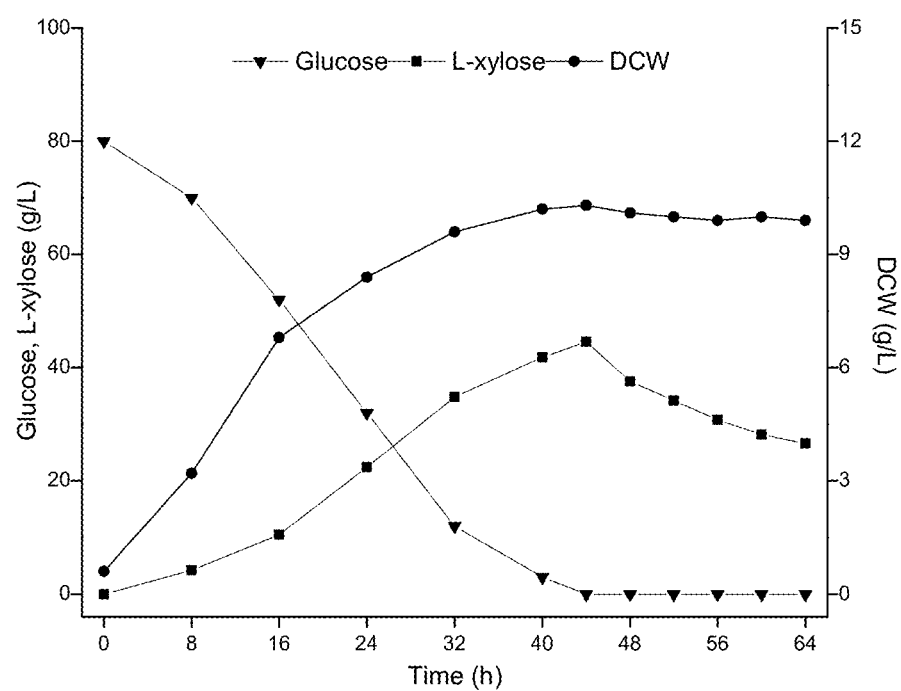
FIG. 3 shows the results of batch fermentation of a recombinant strain *P. plecoglossicida*-2 gadh-25dkg-pdc in a 15 L fermentor.

The yield of L-xylose was determined. The results are shown in FIG. 3. It can be seen that at the 44th h of the fermentation, the total amount of L-xylose produced by the recombinant strain *P. plecoglossicida*-2gadh-25dkg-pdc reached a maximum value of 45.8 g/L, and the glucose transformation rate was 57.3%.

Comparative Example 1 Construction of Recombinant Strain Using Single Plasmid pME6032 Expression Using the strategy of Embodiment 1, a gene of three subunits of a 2-ketogluconate dehydrogenase gene (2GADH), a 2,5-diketogluconate reductase gene and a pyruvate decarboxylase gene were sequentially ligated to a plasmid pME6032 at restriction enzyme cutting sites EcoRI, SacI, KpnI, NcoI, BgiII, and XhoI, a constructed plasmid pME6032-2gadh-25dkg-pdc was expressed in *P. plecoglossicida* CGMCC 7150, and the result shows that the expression is not successful.

Comparative Example 2 Construction of Recombinant Strain Using Single Plasmid pBBR1MCS Expression Using the strategy of Embodiment 1, a gene of three subunits of a 2-ketogluconate dehydrogenase gene (2GADH), a 2,5-diketogluconate reductase gene and a pyruvate decarboxylase gene were sequentially ligated to a plasmid pBBR1MCS at restriction enzyme cutting sites KpnI, XhoI, HindIII, EcoRI, BamHI, and SacI, a constructed plasmid pBBR1MCS-2gadh-25dkg-pdc was expressed in *P. plecoglossicida* CGMCC 7150, and the result shows that the expression is not successful.

Comparative Example 3: Using of 2-ketogluconate dehydrogenase gene (2GADH) Derived from *Erwinia*

An original strain was *P. plecoglossicida* CGMCC 7150, a 2-ketogluconate dehydrogenase gene (2GADH) was derived from *Erwinia*, the remaining steps were the same as in Embodiment 1, and it is found that the 2-ketogluconate dehydrogenase gene (2GADH) derived from *Erwinia* cannot be successfully expressed in a host strain.

Comparative Example 4: Adjustment of Fermentation Medium of Recombinant Strain *P. plecoglossicida*-2gadh-25dkg-pdc The Comparative Example 4 is the same as Embodiment 3, the difference is that the concentrations of glucose, corn steep liquor and urea in a fermentation medium are respectively shown in Table 1 below, and the results show that when the concentrations of glucose, corn steep liquor and urea were 80.0 g/, L4.0 g/L, and 2.0 g/L, respectively, the yield and transformation rate of L-xylose were relatively high, 16.2 g/L and 20.3%, respectively.

TABLE 1

Composition adjustment of fermentation medium and corresponding yield and transformation rate

| No. | Glucose (g/L) | Corn steep liquor (g/L) | Urea (g/L) | L-xylose (g/L) | Transformation rate (100%) |
|---|---|---|---|---|---|
| 1 | 70.0 | 4.0 | 2.0 | 12.0 | 17.1 |
| 2 | 80.0 | 4.0 | 2.0 | 16.2 | 20.3 |
| 3 | 90.0 | 4.0 | 2.0 | 16.4 | 18.2 |
| 4 | 80.0 | 2.0 | 2.0 | 13.5 | 15.9 |
| 5 | 80.0 | 5.0 | 2.0 | 14.0 | 17.5 |
| 6 | 80.0 | 4.0 | 1.0 | 13.4 | 16.8 |
| 7 | 80.0 | 4.0 | 3.0 | 13.0 | 16.3 |

What is claimed is:

1. A recombinant strain for producing L-xylose, comprising nucleic acid sequences for expressing a 2-ketogluconate dehydrogenase gene, a 2,5-diketogluconate reductase gene, and a pyruvate decarboxylase gene, wherein the recombinant strain uses *Pseudomonas plecoglossicida* as a host strain, wherein the 2-ketogluconate dehydrogenase gene comprises nucleic acid sequences for three subunits, which are set forth in SEQ ID NO: 1, SEQ ID NO: 2, and SEQ ID NO: 3, respectively, wherein the 2,5-diketogluconate reductase gene is from *Corynebaterium* ATCC 31090, and wherein the pyruvate decarboxylase gene is from *Saccharomyces cerevisiae*.

2. The recombinant strain according to claim 1, comprising a double plasmid expression system to express the 2-ketogluconate dehydrogenase gene, the 2,5-diketogluconate reductase gene and the pyruvate decarboxylase gene, and the double plasmid expression system comprises a plasmid pME6032 and a plasmid pBBR1MCS-2.

3. The recombinant strain according to claim 2, wherein the plasmid pME6032 is used for expressing the 2-ketogluconate dehydrogenase gene, and the plasmid pBBR1MCS-2 is used for expressing the 2,5-diketogluconate reductase gene and the pyruvate decarboxylase gene.

4. The recombinant strain according to claim 1, wherein the host strain of *Pseudomonas plecoglossicida* is any one selected from a group consisting of *Pseudomonas plecoglossicida* CGMCC 7150, *Pseudomonas plecoglossicida* CGMCC 1.16111, *Pseudomonas plecoglossicida* CGMCC 1.12685, and *Pseudomonas plecoglossicida* CGMCC 1.761.

5. A method for constructing the recombinant strain according to claim 1, comprising the following steps:
(1) simultaneously ligating nucleic acid sequences of gene subunits set forth in SEQ ID NO: 1, SEQ ID NO: 2, and SEQ ID NO: 3 to a vector plasmid to form a first recombinant plasmid;
(2) transforming the first recombinant plasmid obtained in step (1) into *Pseudomonas plecoglossicida* to obtain single plasmid-containing recombinant *Pseudomonas plecoglossicida*;
(3) separately amplifying a 2,5-diketogluconate reductase gene and a pyruvate decarboxylase gene, and simultaneously ligating amplified nucleic acid sequences of the 2,5-diketogluconate reductase gene and the pyruvate decarboxylase gene to an expression vector to form a second recombinant plasmid; and
(4) transforming the second recombinant plasmid obtained in step (3) into the *Pseudomonas plecoglossicida* containing the first recombinant plasmid obtained in step (2) to obtain double plasmid-containing recombinant *Pseudomonas plecoglossicida*.

6. A method of synthesizing L-xylose, comprising: culturing the recombinant strain of claim 1 in a fermentation medium until $OD_{650}$ is 0.6 to 0.8; inducing expression of the 2-ketogluconate dehydrogenase gene, the 2,5-diketogluconate reductase gene and the pyruvate decarboxylase gene; and adding glucose as a substrate; and fermenting for sufficient time for production of L-xylose.

7. The method according to claim 6, wherein the fermentation medium comprises 75.0 to 85.0 g/L of glucose, 3.0 to 4.0 g/L of corn steep liquor, 1.5 to 2.5 g/L of urea, 1.5 to 2.5 g/L of $KH_2PO_4$, 0.4 to 0.6 g/L of $MgSO_4.7H_2O$, and 9.0 to 11.0 g/L of $CaCO_3$, and has a pH value of 6.8.

8. The method according to claim 6, comprising culturing the recombinant strain on a seed medium before fermentation, and the seed medium comprises 14.0 to 15.0 g/L of glucose, 3.5 to 4.0 g/L of corn steep liquor, 1.5 to 2.5 g/L of urea, 1.5 to 2.5 g/L of $KH_2PO_4$, 0.4 to 0.6 g/L of $MgSO_4.7H_2O$, and 0.8 to 1.2 g/L of $CaCO_3$, and has a pH value of 7.0.

* * * * *

SEQUENCE LISTING

<160> NUMBER OF SEQ ID NOS: 13

<210> SEQ ID NO 1
<211> LENGTH: 567
<212> TYPE: DNA
<213> ORGANISM: Artificial Sequence
<220> FEATURE:
<223> OTHER INFORMATION: Synthetic DNA

<400> SEQUENCE: 1

```
atgaacctga aaatcgaacc ggatgttatc ttcagcccga aaaacggcac cggtagcacc      60
cgtcgtgaat ttctgctggc aactgctcgt ttaaccctgg ctggtgcgtt cgcatctctg     120
tctggtaatg cattcgctgc ttctgttgcg cgtgcttctg atccggttac cgcatttatc     180
gctctgtctc gtactatcac cgaacacaaa cagattgatt ctgttttagc agcgcgtttc     240
tttgatgcat tcgcggctcg tgataaacac ttcgcagctc gtctgtctca tctggctcag     300
ctgcagtctc cggatgattc tgcgcagcag ctgctgaaca aagcgaccca ggctggtctg     360
catgattttc tgtatcagat cgttgttgct tggtataccg gtaccgttgg tgatgattac     420
cacggtaccc tggttgctta taaacaggct ttaatgtatc agaccgtttc tgatggcctg     480
attgttccga cctattgtgg taacggtccg atctggtgga ctgctccggt tccggctgaa     540
aacccgtctc tgattgaaaa cctgtaa                                         567
```

<210> SEQ ID NO 2
<211> LENGTH: 1656
<212> TYPE: DNA
<213> ORGANISM: Artificial Sequence
<220> FEATURE:
<223> OTHER INFORMATION: Synthetic DNA

<400> SEQUENCE: 2

```
atgaaaaaac cggttttcac cgcgcagggt gatgctagcg cggatattgt tatcgtgggc      60
tctggtatcg ttgcggtat gatggcaaac gaactggttt ctcagggcta ttctgtgctg     120
gttctggaag cgggtctgcg tatcgatcgc gcccaggccg ttgaaaactg gcgtaacatg     180
ccgtttgcga accgtgcagg cagcgatttc cagggtctgt atccgcagtc caaattcgcg     240
ccggcgccgc tgtacttccc acgtaacaac tacgttaacg ttaccggccc gaacgcggat     300
```

```
tccttccagc agggttacct gcgtaccgtt ggtggtacca cgtggcactg ggcggcgagc    360
tgctggcgtc accacccgag cgatttcgtg atgcagtcca aatacggtgt tggtcgtgat    420
tggccaatcg gctatgatga actggaaccg tggtactgca aagcagaaaa cgaaatcggt    480
gttgctggcc cgaacgaccc ggcgcgtcag agcccgaccg aacgtagcca gccgtatccg    540
atggatatgg tgccgttcgc acacggtgat aactacttcg cgtccgttgt aacccgcat     600
ggctacaacc tggttccgat ccgcagggc cgttccaccc gtccgtggga aggtcgtccg     660
acctgctgcg gcaacaacaa ctgtcagccg atctgtccga tcggtgcgat gtacaacggt    720
atccaccacg ttgaacgtgc ggaacgtaac ggcgcggtgg tgctggcaga agctgttgtt    780
tacaagatgg ataccgattc caacaaccgt attaccgctg tacactggct ggacaccagt    840
ggcgcaagcc acaaagccac cgctaaagcg tttgcgctgg cgtgtaacgg tatcgaaacc    900
ccgcgtctgc tgctgatggc tgcgaacgat gcgaacccga cggcattgc caacgcgagc     960
gatatggttg ccgtaatat gatggaccat agcggtttc actgtagctt cctgaccaaa     1020
gagccggttt ggctgggtaa aggtccgcg cagtcttcct gcatggtggg ctaccgtgac    1080
ggtgatttcc gtcgtgatta cagcgcaaac aaagttatcc tgaacaacat ctctcgtgtt    1140
gttaccgcga cccaacaggc catgaaaaaa ggtctggttg gcaaagctct ggatgaagaa    1200
atccgttatc gtgcggttca cagcgtggat ctgtccatct ctctggaacc gctgccggac    1260
ccggaaaacc gtctgaccct gtctaaaacc gtaaagatc cgcacggcct gccgtgcccg    1320
gacatctact acgatgttgg tgactacgtt cgtaaaggtg cggaagcgtc ccatgcgcag    1380
ctggaacata tcgccagct gtttgatgcg aaagagttta ccatttctca gggtctgaac    1440
gctaacaacc acattatggg tggtgttatc atgggcaaaa acgcaaaaga gcggttgtt    1500
gatggtaact gtcgtgcgtt cgatcacgaa aacctgtggc tgccgggtgg tggcgcgatc    1560
ccgtctgctt ctgtggttaa cagcacctg actatggcgg cgctgggtct gaaagcggct    1620
cacgatatca gcctgcgtat gaaaggtgat gcatga                              1656

<210> SEQ ID NO 3
<211> LENGTH: 1413
<212> TYPE: DNA
<213> ORGANISM: Artificial Sequence
<220> FEATURE:
<223> OTHER INFORMATION: Synthetic DNA

<400> SEQUENCE: 3
atgaaacagc tgctgatggc aaccagcctg atgctgctc tgaccctgtc tgctccggca     60
gaacagactg acctgaccct gttgcgccag ggcgaacaag tcgccattgc ttccgattgt    120
caggcatgcc acaccgcgcc gggtagcgcg accgcgttct ccggtggcta cgcgatcgcg    180
tcccgatgg gcgtgatcta ctctaccaat atcaccccga gcgcggatgg tatcggcccg    240
tactctgaag cggaatttc ccaggcggtg cgtcacggcg tgcgtgcgga tggcgcgcag    300
ctgtacccgg cgatgccgta cacctcttat agcaaaatca ctgacgaaga tctgcatgct    360
ctgtactact acttcatgca cggcgttaaa ccggtggaac agaaaaaccg ccagaccagc    420
ctgccgttcc cgttcaacct gcgtttctcc atgttcttct ggaacctgat gttcgcggat    480
gataaaccgt acctgagcga tgatagccag tctgctgaat ggaaccgtgg taactacctg    540
gtgaacggcc tggcgcactg caacacctgc cacaccccgc gtggcgttct gatgcaggaa    600
gcaggtaacc gcccgctggc gggtgcgccg attggtagct ggtacgctcc gaacattacc    660
tccgatgcga tcagcggcat cggtggttgg cgtaacgatg aactggtgca gtacctgaaa    720
```

-continued

```
accggccgtg cggaaggtaa aaaccaggcg gcaggtggta tggcggaagc ggttgaacac    780
tctctgcagt acctgagcga tagcgatctg aaagcgattg cggtttatct gaaaagcacc    840
accccgattc gtgatgaagg tgatacccag ccggcgtact ccttcggtaa accggcggat    900
gttgaaaaca gcatccgcgg tcgtaacgcc aacaacgcta accactctct gaccaacggt    960
gctgcgctgt tctctggcaa ctgcgcgtct tgccaccagc cggatggcgc gggctctgca   1020
aatcaggcgt atccgtctct gttccacaac accgccaccg gcatgcataa cccggcgaac   1080
ctgattgcgg cgatcctgtt cggcgttcag cgtaacaccg ctgcgggcca ggtcctgatg   1140
ccgggattta gtagcccatc ttacgtagat aaattgagtg acgcacaggt agcagacatt   1200
agtaatttcg ttctggcgca ctatggtaac ccggaagtta ccgtttctgc aggtgatgtt   1260
gcgtgggttc gtcagggcgg ccacccgccg ctgctggcgc gtgcgcagcc gtggatcatg   1320
ccgggcatcg tggcgctgat cgtgatcctg ctggcggttt gcgcgggtct gacctggcgt   1380
cgtcgtcgtc gtatcgcgcg tgataacggt taa                                1413
```

<210> SEQ ID NO 4
<211> LENGTH: 33
<212> TYPE: DNA
<213> ORGANISM: Artificial Sequence
<220> FEATURE:
<223> OTHER INFORMATION: Synthetic DNA

<400> SEQUENCE: 4
cgcggatccg atgaacctga aaatcgaacc gga                                  33

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
cccaagcttt tacaggtttt caatcagaga cgg                                  33

<210> SEQ ID NO 6
<211> LENGTH: 34
<212> TYPE: DNA
<213> ORGANISM: Artificial Sequence
<220> FEATURE:
<223> OTHER INFORMATION: Synthetic DNA

<400> SEQUENCE: 6
cgcggatccg atgaaaaaac cggttttcac cgcg                                 34

<210> SEQ ID NO 7
<211> LENGTH: 35
<212> TYPE: DNA
<213> ORGANISM: Artificial Sequence
<220> FEATURE:
<223> OTHER INFORMATION: Synthetic DNA

<400> SEQUENCE: 7
cccaagcttt catgcatcac ctttcatacg caggc                                35

<210> SEQ ID NO 8
<211> LENGTH: 32
<212> TYPE: DNA
<213> ORGANISM: Artificial Sequence
<220> FEATURE:

```
<223> OTHER INFORMATION: Synthetic DNA

<400> SEQUENCE: 8
cgcggatccg atgaaacagc tgctgatggc aa                                      32

<210> SEQ ID NO 9
<211> LENGTH: 29
<212> TYPE: DNA
<213> ORGANISM: Artificial Sequence
<220> FEATURE:
<223> OTHER INFORMATION: Synthetic DNA

<400> SEQUENCE: 9
cccaagcttt taaccgttat cacgcgcga                                          29

<210> SEQ ID NO 10
<211> LENGTH: 44
<212> TYPE: DNA
<213> ORGANISM: Artificial Sequence
<220> FEATURE:
<223> OTHER INFORMATION: Synthetic DNA

<400> SEQUENCE: 10
cgcggatccg atgaatctaa aaatcgaacc cgacgtaatt tttt                         44

<210> SEQ ID NO 11
<211> LENGTH: 33
<212> TYPE: DNA
<213> ORGANISM: Artificial Sequence
<220> FEATURE:
<223> OTHER INFORMATION: Synthetic DNA

<400> SEQUENCE: 11
acgcgtcgac tcatccattg tctcgggcta tcc                                     33

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
catgccatgg attcaattac tttgggtaaa tatttgttcg                              40

<210> SEQ ID NO 13
<211> LENGTH: 34
<212> TYPE: DNA
<213> ORGANISM: Artificial Sequence
<220> FEATURE:
<223> OTHER INFORMATION: Synthetic DNA

<400> SEQUENCE: 13
ccgctcgagt tgcttagcgt tggtagcagc agtc                                    34
```